United States Patent [19]
Blaseio

[11] Patent Number: 6,058,200
[45] Date of Patent: *May 2, 2000

[54] METHOD OF MANIPULATING CEPHALOMETRIC LINE TRACINGS

[76] Inventor: Gunther Blaseio, 1001 B Ave. Suite 206, Coronado, Calif. 92118

[*] Notice: This patent issued on a continued prosecution application filed under 37 CFR 1.53(d), and is subject to the twenty year patent term provisions of 35 U.S.C. 154(a)(2).

[21] Appl. No.: 08/853,321

[22] Filed: May 8, 1997

Related U.S. Application Data

[60] Provisional application No. 60/017,515, May 10, 1996.
[51] Int. Cl.[7] .................................................. G06K 9/00
[52] U.S. Cl. ........................ 382/100; 382/115; 382/295
[58] Field of Search .................................. 382/100, 115, 382/118, 201, 203, 296, 293, 295; 345/441, 442; 433/68

[56] References Cited

U.S. PATENT DOCUMENTS

| | | | |
|---|---|---|---|
| 5,278,756 | 1/1994 | Lemchen et al. | 364/413.28 |
| 5,576,778 | 11/1996 | Fujie et al. | 351/177 |
| 5,683,243 | 11/1997 | Andreiko et al. | 433/3 |
| 5,687,259 | 11/1997 | Linford | 382/294 |

OTHER PUBLICATIONS

Blaseio, Gunther, Quick Ceph Image, Reference Guide, 1993.

*Primary Examiner*—Yon J. Couso
*Attorney, Agent, or Firm*—Merle W. Richman, III

[57] ABSTRACT

A method for producing a cephalometric lateral profile usable for growth forecasts and treatment simulations particularly for use by orthodontists and maxillo-facial surgeons in planning treatments for their patients. The method includes obtaining a lateral cephalometric x-ray and image of a subject, e.g. by an x-ray machine and a video camera, creating a polyline outline of the lateral profile of the image, identifying a set of pre-defined points on the outline, and converting the polyline outline to a corresponding series of Bezier curves using the identified points as anchor points. The pre-defined points preferably include a set of points on the polyline outline at which the ratio of the subject's soft tissue to the subject's hard tissue is known, e.g. the glabella, the soft nasion, the tip of the nose, the subnasal, the soft A-point, the upper lip, the upper lip embrasure, the lower lip embrasure, the lower lip, the soft B-point, the chin, and the soft menton. Preferably the step of creating a polyline outline is done by digitizing the lateral profile of the cephalometric image and providing the digital values to a processor. The processor then identifies the set of anchor points by using certain correspondingly unique geographical characteristics of the points. The method can also include the step of eliminating surplusage digital values which can arise from the digitizing.

16 Claims, 2 Drawing Sheets

METHOD OF MANIPULATING CEPHALOMETRIC LINE TRACINGS

This application claims the benefit of U.S. Provisional Application No. 60/017,515, filed May 10, 1996.

BACKGROUND OF THE INVENTION

This invention relates in general to processes for manipulating cephalometric images, and in particular to processes for interactively manipulating cephalometric line tracings to produce growth forecasts and treatment simulations particularly for use by orthodontists and maxillo-facial surgeons in planning treatments for their patients.

The prior art includes a computer program entitled QUICK CEPH IMAGE which allows a user to interactively generate growth forecasts and treatment simulations on line tracings and real images of patients. This included the steps of (1) recording a cephalometric image of a patient, such as a lateral view of the profile, maxilla and mandible of the patient, into a computer, (2) digitizing a plurality of landmarks on the cephalometric image to produce a tracing, (3) manipulating the tracing by moving hard tissue to show soft tissue changes, and (4) morphing the image to follow the new tracing. As used herein the term "morphing" refers to computerized image manipulation. The program can automatically generate a tracing and measurements for a chosen analysis. The program also produces growth forecasts, and allows a user to simulate the effects of a treatment by manipulating the tracing. By actuating a morphing function the program can revise a captured image to follow a new tracing instantly.

The prior art uses a plurality of straight lines or vectors to define the line tracings. This invention improves upon the prior art by implementing Bezier curves to improve the line tracings. The method of this invention provides a profound improvement in quality.

SUMMARY OF THE INVENTION

An object of this invention is to provide a cephalometric lateral profile that is extremely crisp and smooth.

A further object of this invention is to provide a cephalometric lateral profile, as above, which is easily edited but yet precise, especially for growth forecasts and treatment simulations.

A further object of this invention is to provide a cephalometric lateral profile, as above, which is more adaptable to morphing than is presently available in the prior art.

A further object of this invention is to provide a cephalometric lateral profile, as above, without kinks or corners.

These objects, and other objects expressed or implied in this document, are accomplished by a method for producing a cephalometric lateral profile usable for a growth forecast and/or treatment simulation, the method comprising the steps: obtaining a lateral cephalometric image of a subject; creating a polyline outline of the lateral profile of the image; identifying a set of pre-defined points on the outline; and converting the polyline outline to a corresponding series of Bezier curves using the identified points as anchor points. The pre-defined points preferably includes a point on the polyline outline at which the ratio of the subject's soft tissue to the subject's hard tissue is known, e.g. the glabella, the soft nasion, the tip of the nose, the subnasal, the soft A-point, the upper lip, the upper lip embrasure, the lower lip embrasure, the lower lip, the soft B-point, the chin, and the soft menton. Preferably the step of creating a polyline outline is done by digitizing the lateral profile of the cephalometric image and providing the digitized points to a processor. The processor then identifies the set of pre-defined points by using certain correspondingly unique geographical characteristics of the points. The method can also include the step of eliminating surplusage digital values from the digitizing.

DESCRIPTION OF THE PREFERRED EMBODIMENT

Figure 1:
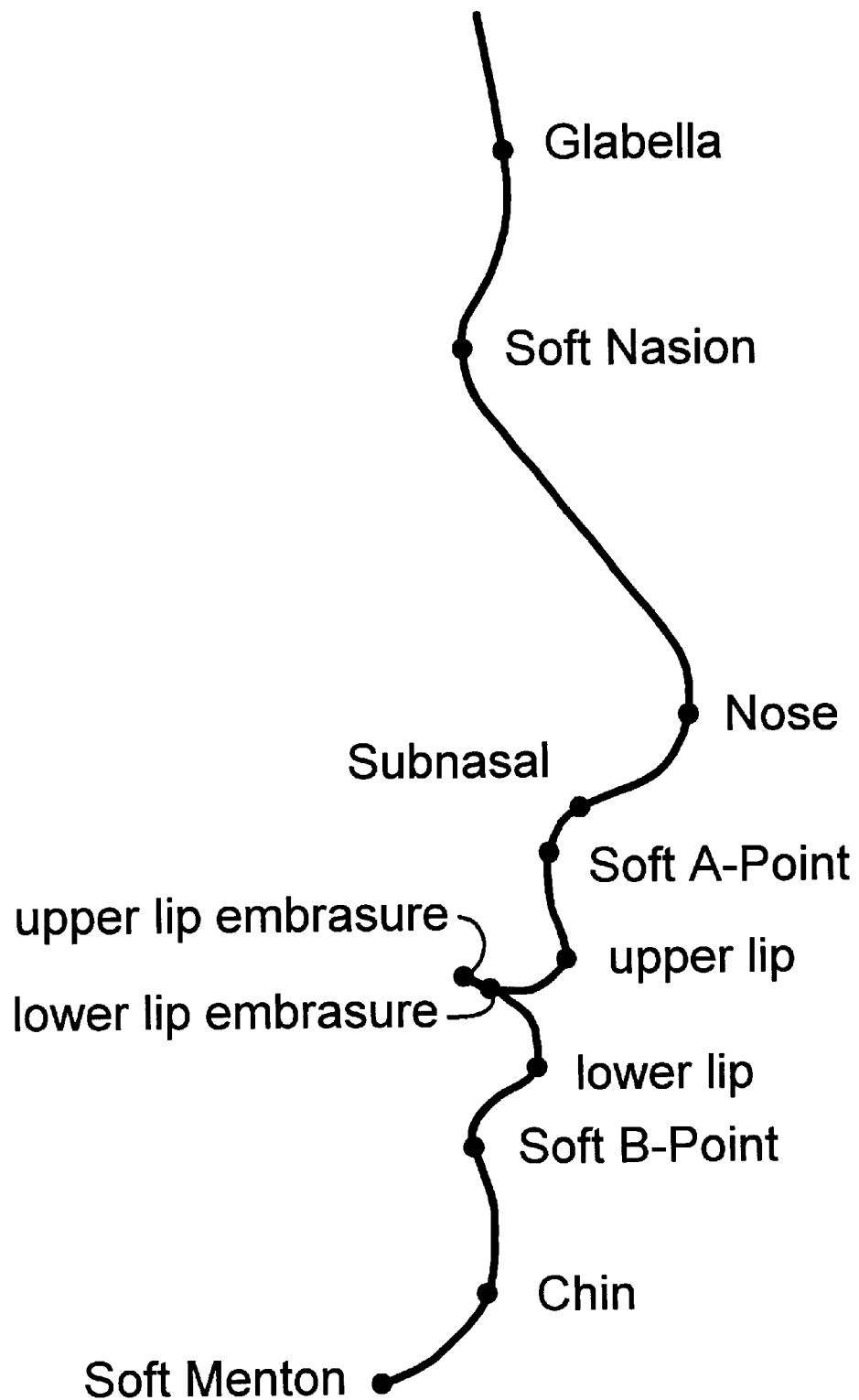
FIG. 1 is an outline, formed according to this invention, of a lateral cephalometric view of a patient's head showing certain pre-defined Bezier curve anchor points according to this invention.

Referring to FIG. 1, illustrated is a line tracing depicting a lateral profile outline of a lateral cephalometric view. On the tracing are a preferred set of anchor points for use by an algorithm which produces a set of Bezier curves based upon these anchor points. Basically, a Bezier curve is a curved segment that is determined by start and end points, i.e. anchor points, and control points which define the curvature or shape of the segment. Algorithms for producing a series of Bezier curves from a set of polylines are well known in the art. The result of the method of this invention is a high quality line tracing comprised of a series of Bezier curves.

The key to a meaningful orthodontic and surgical treatment simulation is the possibility to interactively manipulate curves in tracings of x-rays and photos. Simply converting digitized outlines (polylines) into mathematical curves (NURBS) does not enable the diagnostic software to automatically move soft tissue in a predetermined ratio to the hard tissue because these ratios are only known in specific locations such as Glabella, Tip of Nose, A-Point, Tip of Upper Lip, Tip of Lower Lip, B-Point, Chin, Menton, etc. This invention forces the Bezier conversion algorithm into using these pre-defined points, which are preferably automatically located on the tracings by another algorithm, as the anchor points of Bezier curve segments, a special case of NURBS. This effectively allows the automatic and interactive manipulation of hard and soft tissue structures within the context known to the profession.

This invention preferably includes a computerized algorithm to automatically locate the preferred anchor points. The algorithm takes advantage of certain unique geographical characteristic of the points to locate them. Referring again to FIG. 1, the Glabella is the most prominent point in the midsaggital plane of the forehead. The soft Nasion is the deepest depression at the root of the nose in the midsaggital plane. The Nose is the most anterior projection point of the nose. The Subnasal is the point at which the columella merges with the upper cutaneous lip in the midsaggital plane. The soft A-point is the deepest depression between subnasal and the tip of the upper lip. The upper lip is the most prominent point in the midsaggital plane of the upper lip. The upper lip embrasure is the end point of the upper lip. The lower lip embrasure is the end point of the lower lip. The lower lip is the most prominent point in the midsaggital plane of the lower lip. The soft B-point is the deepest depression between the tip of the upper lip and the chin. The Chin is the most anterior point of the chin, also called soft Pogonion. The soft Menton is the lowest most contour point of the soft tissue mandibular symphysis. However, any other method of precisely locating these points can be used.

Figure 2:
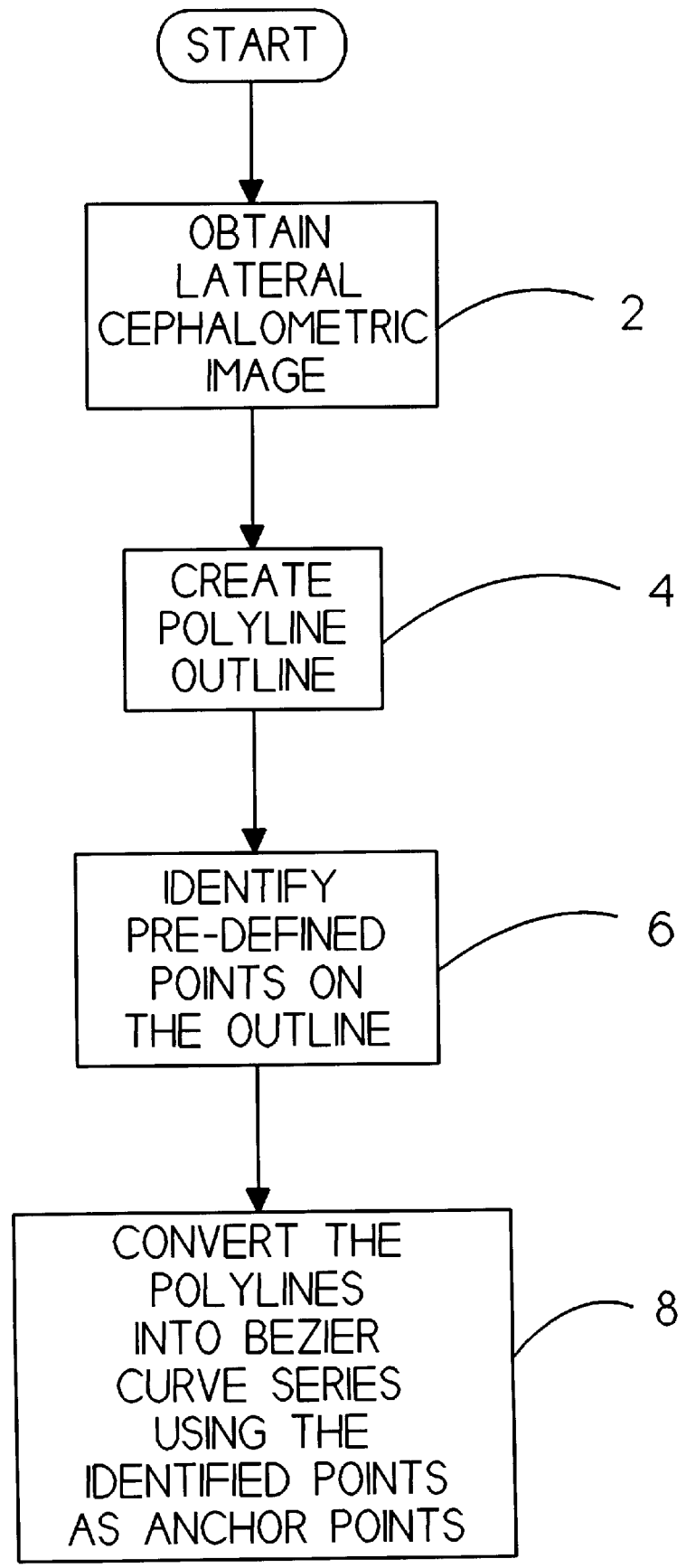
FIG. 2 is a flow chart of the method used to derive the outline on FIG. 1.

Referring to FIG. 2, this invention includes as a first step, obtaining a lateral cephalometric image 2 of a subject, e.g. by an x-ray machine and a video camera, which is preferably captured directly to a processor, such as a computer. Then a polyline outline of the lateral profile of the subject is created 4 from the lateral cephalometric image, e.g. by hand tracing over the image using a digitizer or a mouse. Then certain pre-defined points on the outline or tracing are identified 6, i.e. located (preferably by a computerized algorithm). In the preferred method, the points include the: Glabella, soft Nasion, tip of nose, subnasal, soft A-Point, tip of upper lip, upper lip embrasure, lower lip embrasure, tip of lower lip, soft B-Point, chin, and soft Menton. Then the polylines are converted 8 into a series of connected Bezier curves using the identified points as anchor points (start and end points of the segments). The locations of control points of the Bezier curve segments (which locate tangent lines that define the shape and direction of the curve segments) are selected to best fit the segments to the polyline tracing.

Since the unconverted polyline outline is defined by a set of digitized points and typically there are a surplusage of points, this invention can also include the step of eliminating extraneous points. For example, this method of this invention can eliminate points until the tracing is defined by points about 3 mm apart.

This invention allows computerized manipulation of curved lines rather than multiple small straight lines to draw, manipulate and store the outlines of soft tissue structures and bones. This improvement has resulted in a profound quality improvement in growth forecasts and treatment simulations. The immediate benefits of the usage of curves produced according to this invention are:

1. Profile and bone outlines are extremely crisp and smooth, smoother in fact than would be possible with any hand drawing.
2. Editing of curves is very easy, flexible and precise.
3. Growth forecast is more reliable.
4. Treatment simulation creates smooth tracings without kinks or corners.
5. Treatment simulation is more reliable.
6. Morphed images demonstrate a fourfold increase in details.

The foregoing description and drawings were given for illustrative purposes only, it being understood that the invention is not limited to the embodiments disclosed, but is intended to embrace any and all alternatives, equivalents, modifications and rearrangements of elements falling within the scope of the invention as defined by the following claims. For example, the above described set of anchor points is not the only set that can be used, but rather is only the preferred set which has been found to be optimal for the purposes of this invention. More or fewer points can be used depending, inter alia, on the degree of precision desired.

I claim:

1. Method for producing a growth forecast or treatment simulation for the head of a patient, the method comprising the steps of:
   (a) obtaining a hard tissue and soft tissue image representing the hard tissue structure and soft tissue structure of the head of the patient;
   (b) identifying a set of pre-defined hard tissue points on the hard tissue image where the position of a set of soft tissue points on the soft tissue image is known relative the position of the set of pre-defined hard tissue points;
   (c) manipulating the position of at least one of the set of pre-defined hard tissue points;
   (d) determining the set of soft tissue points based on the set of pre-defined hard tissue points after the manipulation of the position of the at least one of the set of pre-defined hard tissue points; and
   (e) generating a soft tissue tracing representing the soft tissue structure of the patient by generating a series of Bezier curves having the set of determined soft tissue points as anchor points,
   (f) wherein the soft tissue tracing formed from the series of Bezier curves represents the growth forecast or the treatment simulation of the head of the patient based on the manipulation of the position of the at least one of the set of pre-defined hard tissue points.

2. The method according to claim 1, wherein the set of pre-defined hard tissue points includes one of the glabella, the soft nasion, the tip of the nose, the subnasal, the soft A-point, the most prominent point in the midsaggital plane of the upper lip, the upper lip embrasure, the lower lip embrasure, the most prominent point in the midsaggital plan of the lower lip, the soft B-point, the most anterior point of the chin, and the soft menton.

3. The method according to claim 1, wherein the set of pre-defined hard tissue points is identified by certain correspondingly unique geographical characteristics.

4. The method according to claim 1 wherein the set of points comprises the glabella, the soft nasion, the tip of the nose, the subnasal, the soft A-point, the upper lip, the upper lip embrasure, the lower lip embrasure, the lower lip, the soft B-point, the chin, and the soft menton.

5. The method according to claim 1, wherein step (b) includes the steps of:
   (i) generating a hard tissue tracing representing the hard tissue structure of the patient; and
   (ii) identifying a set of pre-defined hard tissue points on the hard tissue tracing.

6. The method according to claim 1, wherein step (b) includes the steps of:
   (iii) generating a hard tissue tracing representing the hard tissue structure of the patient; and
   (i) identifying a set of pre-defined hard tissue points on the hard tissue tracing; and
   (ii) generating a generating a hard tissue tracing representing the hard tissue structure of the patient by generating a series of Bezier curves having the set of pre-defined hard tissue points as anchor points.

7. The method according to claim 1, wherein step (b) includes the steps of:
   (i) identifying a set of pre-defined hard tissue points on the hard tissue image; and
   (ii) generating a generating a hard tissue tracing representing the hard tissue structure of the patient by generating a series of Bezier curves having the set of pre-defined hard tissue points as anchor points.

8. The method according to claim 5, wherein the step of generating a hard tissue tracing representing the hard tissue structure of the patient comprises the step of digitizing the hard tissue image and providing the digitized points to a processor, and wherein the step of identifying the set of pre-defined hard tissue points is done by the processor using certain correspondingly unique geographical characteristics of the points.

9. The method according to claim 6, wherein the step of generating a hard tissue tracing representing the hard tissue structure of the patient comprises the step of digitizing the hard tissue image and providing the digitized points to a processor, and wherein the step of identifying the set of pre-defined hard tissue points is done by the processor using certain correspondingly unique geographical characteristics of the points.

10. The method according to claim 8 further comprising the step of eliminating surplusage digital values.

11. The method according to claim 5, wherein the set of pre-defined hard tissue points is identified by certain correspondingly unique geographical characteristics.

12. The method according to claim 6, wherein the set of pre-defined hard tissue points is identified by certain correspondingly unique geographical characteristics.

13. The method according to claim 7, wherein the set of pre-defined hard tissue points is identified by certain correspondingly unique geographical characteristics.

14. The method according to claim 5, wherein the set of pre-defined hard tissue points includes one of the soft B-point, the glabella, the soft nasion, the tip of the nose, the subnasal, the soft A-point, the most prominent point in the midsaggital plane of the upper lip, the upper lip embrasure, the lower lip embrasure, the most prominent point in the midsaggital plan of the lower lip, the most anterior point of the chin, and the soft menton.

15. The method according to claim 6, wherein the set of pre-defined hard tissue points includes one of the most anterior point of the chin, the glabella, the soft nasion, the tip of the nose, the subnasal, the soft A-point, the most prominent point in the midsaggital plane of the upper lip, the upper lip embrasure, the lower lip embrasure, the most prominent point in the midsaggital plan of the lower lip, the soft B-point, and the soft menton.

16. The method according to claim 7, wherein the set of pre-defined hard tissue points includes one of the glabella, the soft nasion, the tip of the nose, the subnasal, the soft A-point, the most prominent point in the midsaggital plane of the upper lip, the upper lip embrasure, the lower lip embrasure, the most prominent point in the midsaggital plan of the lower lip, the soft B-point, the most anterior point of the chin, and the soft menton.

\* \* \* \* \*